United States Patent [19]

Butler et al.

[11] Patent Number: 4,466,905

[45] Date of Patent: Aug. 21, 1984

[54] POLYMERIZATION INHIBITION PROCESS FOR VINYL AROMATIC COMPOUNDS

[75] Inventors: James R. Butler; James M. Watson; Debra L. Kendall, all of Big Spring; Karen A. Mikkelson, Lubbock, all of Tex.

[73] Assignee: Cosden Technology, Inc., Dallas, Tex.

[21] Appl. No.: 483,978

[22] Filed: Apr. 11, 1983

[51] Int. Cl.³ .................. C09K 15/22; C08F 2/38
[52] U.S. Cl. ............................ 252/403; 526/83; 526/84; 526/85
[58] Field of Search .................. 252/403; 526/83–85

[56] References Cited

U.S. PATENT DOCUMENTS

| 2,064,571 | 12/1936 | Smith | 203/9 |
|---|---|---|---|
| 2,388,041 | 10/1945 | Craig | 203/9 |
| 2,394,756 | 2/1946 | Dreisbach | 526/84 |
| 2,399,340 | 4/1946 | Franz | 203/9 |
| 3,366,702 | 1/1968 | Moriarity | 203/9 |
| 3,654,129 | 4/1972 | Bloch | 203/9 |
| 3,674,651 | 7/1972 | Otsuki et al. | 203/59 |
| 4,061,545 | 12/1977 | Watson | 203/49 |
| 4,177,110 | 12/1979 | Watson | 203/49 |
| 4,220,743 | 9/1980 | Englin | 526/62 |
| 4,343,956 | 8/1982 | Jackish | 252/403 |
| 4,346,202 | 8/1982 | Cohen | 526/85 |

OTHER PUBLICATIONS

Chem. Abstract, 82, 140737p (1975).
Chem. Abstract, 88, 388021 (1978).
Chem. Abstract, 75, 112851h (1971).
Chem. Abstract, 75, 107782g (1971).

Primary Examiner—Christine M. Nucker
Attorney, Agent, or Firm—Robert H. Sproule; M. Norwood Cheairs

[57] ABSTRACT

A compound and a process for utilizing the compound to prevent the polymerization of vinyl aromatic compounds, such as styrene, during heating. The composition includes effective amounts of 2,6-dinitro-p-cresol and either a phenylenediamine or 4-tert-butylcatechol respectively, to act as a polymerization co-inhibitor system in the presence of oxygen.

10 Claims, 2 Drawing Figures

POLYMERIZATION INHIBITION PROCESS FOR VINYL AROMATIC COMPOUNDS

BACKGROUND OF THE INVENTION

The present invention relates to a polymer inhibiting composition and to a process for inhibiting the polymerization of a readily polymerizable vinyl aromatic compound.

It is well known that vinyl aromatic compounds such as monomeric styrene, lower alkylated styrene such as alpha-methylstyrene and the like, polymerize readily and furthermore, that the rate of polymerization increases with increasing temperature. Inasmuch as vinyl aromatic compounds produced by common industrial methods contain impurities, these compounds must be subjected to separation and purification processes in order to be suitable for most types of further industrial use. Such separation and purification are generally accomplished by distillation.

In order to prevent polymerization during storage of vinyl aromatic compounds, various types of known polymerization inhibitors have been employed usually under refrigerated conditions. For example, common inhibitors useful for inhibiting the polymerization of vinyl aromatic compounds during storage conditions include 4-tert-butylcatechol (TBC) and hydroquinone.

Sulfur, on the other hand, has been widely employed as a polymerization inhibitor during the distillation of various vinyl aromatic compounds. However, while sulfur provides a reasonably effective inhibitor, its use in such distillation processes results in a highly significant disadvantage namely, there is formed in the reboiler bottom of the distillation column a valueless waste material highly contaminated with sulfur. This waste material, furthermore represents a significant problem of pollution and/or waste removal.

Although many compounds are effective for inhibiting the polymerization of vinyl aromatic compounds under differing conditions such as storage, only some of these compounds have proved to be of any real utility for inhibiting vinyl aromatic polymerization under distillation conditions. One compound found effective for polymerization inhibition is 2,6-dinitro-p-cresol (DNPC) disclosed in U.S. Pat. No. 4,105,506 by Watson. In addition, it has been found that previously known polymerization inhibitors may be combined to achieve an inhibitory effect greater than either inhibitor alone. The synergistic effect of combining two known inhibitors was disclosed in U.S. Pat. No. 4,061,545 by Watson, wherein phenothiazine and tert-butylcatechol (TBC) were used together in the presence of oxygen as a polymerization inhibitor. The synergistic effect of N-nitrosodiphenylamine combined with DNPC in inhibiting the polymerization of vinyl toluene under vacuum conditions was disclosed in U.S. Pat. No. 4,341,600 by Watson. It has been found, however, that as the distillation temperature increases, the effectiveness of these inhibitors decreases.

During distillation of vinyl aromatic compounds, higher distillation temperatures are preferred in a distillation apparatus in order to achieve a higher throughput and a more energy efficient distillation. These higher temperatures, however, also result in an increased rate of polymerization which leads to unacceptable levels of polymer in the distillation apparatus. Accordingly, therefore, there exists a strong need for a polymerization inhibitor which will effectively prevent the polymerization of vinyl aromatic compounds during distillation at higher temperatures.

SUMMARY OF THE INVENTION

It is therefore an object of the present invention to provide both a polymer inhibiting composition and a process for inhibiting the polymerization of vinyl aromatic compounds.

Another object of the invention is to provide both a polymer inhibiting composition and a process for inhibiting the polymerization of vinyl aromatic compounds at higher temperatures resulting in a higher recovery of high purity, unsaturated vinyl aromatic compounds and in the production of less undesirable by-products.

A still further object of the invention resides in the provision of both a polymer inhibiting composition and a process for inhibiting the polymerization of vinyl aromatic compounds which permits the distillation apparatus to be operated at a higher temperature and an increased rate of throughput without a reduction in efficiency.

In accomplishing the foregoing and other objects, there has been provided in accordance with the present invention a composition for inhibiting the distillation of a readily polymerizable vinyl aromatic compound in the presence of oxygen when subject to elevated temperature such as in a distillation process, the composition comprising an effective amount of 2,6-dinitro-p-cresol and an effective amount of a phenylene diamine having the formula

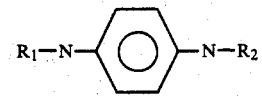

wherein $R_1$ and $R_2$ are alkyl, aryl or hydrogen.

In an alternate embodiment, the inhibitor composition comprises an effective amount of 2,6-dinitro-p-cresol and 4-tert-butylcatechol.

The vinyl aromatic compounds covered in the present invention include styrene, substituted styrene, divinylbenzene, vinyltoluene, vinyl naphthalene and the polyvinylbenzenes. This group is also understood to include all structural isomers thereof.

Also, in accomplishing the foregoing other objects, there is provided in accordance with the present invention, a process for inhibiting the polymerization of a readily polymerizable vinyl aromatic compound comprising subjecting the vinyl aromatic compound to heating conditions, such as distillation, in the presence of effective amounts of 2,6-dinitro-p-cresol and the aforementioned phenylenediamine derivatives or 4-tert-butylcatechol respectively, and oxygen.

According to the present process, the amount of polymerization occurring within the distillation apparatus at temperatures as high as 150° C. is significantly reduced in comparison with conventionally employed methods. In addition, the distillation apparatus may be operated at a higher temperature and pressure than when using conventional inhibitors thereby allowing a higher rate of distillation throughput.

Further objects, features, and advantages of the invention will become apparent from the detailed description which follows and from the claims.

DETAILED DESCRIPTION OF THE PREFERRED EMBODIMENT

Figure 1:
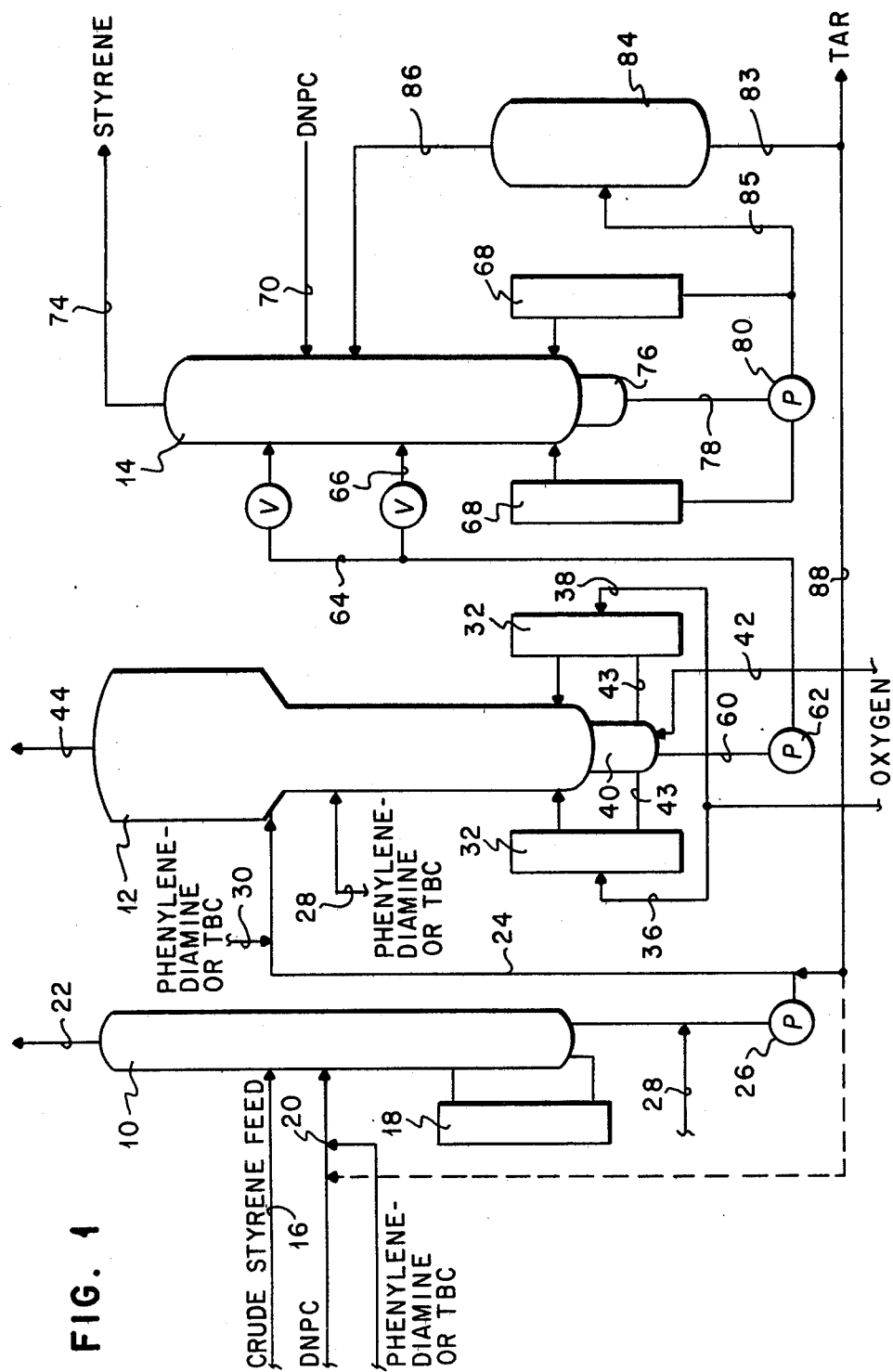
FIG. 1 is a schematic diagram of one embodiment of the process of the present invention utilizing a three column distillation train.

The present invention employs 2,6-dinitro-p-cresol, hereinafter referred to as DNPC, and a phenylenediamine derivative in the presence of oxygen, as a polymerization co-inhibitor composition during the heating of vinyl aromatic compounds.

The phenylenediamine of the present invention has the formula:

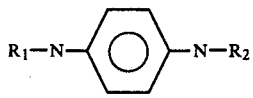

wherein $R_1$ is an alkyl group, aryl group or hydrogen, and $R_2$ is an alkyl group, aryl group, or hydrogen. It is preferred that the alkyl groups of $R_1$ and $R_2$ respectively contain from 1 to 12 carbons inclusive. Examples of such preferred phenylenediamine derivatives include p-phenylenediamine, N,N'dimethyl phenylenediamine, N,N'-diethylphenylenediamine, N,N'-Bis(1,4-dimethylpentyl)-p-phenylenediamine, and N-4-methyl-2-pentyl-N'-phenyl-p-phenylenediamine.

It should be noted that N,N'-Bis(1,4-dimethylpentyl)-p-phenylenediamine and N-4-methyl-2-pentyl-N'-phenyl-p-phenylenediamine are particularly preferred; however, N,N'-Bis(1,4-dimethylpentyl)-p-phenylenediamine is the most preferred.

The distillation techniques of the present invention are suitable for use in virtually any type of separation of a readily polymerizable vinyl aromatic compound from a mixture where the compound is subjected to temperatures above room temperature. By polymerization inhibitor it is meant that unwanted polymerization of the vinyl aromatic monomer is prevented at elevated temperatures such as in a distillative apparatus. Increasing the temperature in the apparatus has the advantages of a higher distillation rate, however, this increased temperature can cause a higher rate of polymerization which is counterbalanced by the introduction of the inhibitor of the present invention. In its most useful application, the composition is applied to a distillation mixture of vinyl aromatic compounds selected from the group consisting of styrene, substituted styrene such as alpha-methyl styrene, divinylbenzene, vinyl toluene, vinyl naphthalene, and the polyvinylbenzenes. This group is understood to include all structural isomers of the aforementioned compounds. The preferred application of the present invention relates to the distillation of crude styrene.

The amounts of polymerization inhibitor added may vary over a wide range depending upon the conditions of distillation. Generally, the degree of stabilization is proportional to the amount of inhibitor added. In accordance with the present invention, it has been found, based on vinyl aromatic feed to the B-T column 10 or the recycle column 90, that a phenylenediamine concentration generally between about 50 ppm and 2000 ppm and a DNPC concentration between about 100 ppm and 2000 ppm have generally produced suitable results, depending primarily upon the temperature of the distillative mixture and the degree of inhibition desired. Preferably however, the phenylenediamine inhibitor of the present invention is used in concentration from about 50 ppm to about 1000 ppm and the DNPC concentration is from about 250 ppm to about 1000 ppm. The preferred ppm ratio of phenylenediamine to DNPC is 2:3. There is no particular order for mixing the compounds of the present invention. In one particular embodiment they are added together at atmospheric temperature and pressure outside the distillation train and injected therein. The distillation technique of the present invention is suitable for use in virtually any type of distillative separation of a readily polymerizable vinyl aromatic compound from a mixture wherein the vinyl aromatic compound is subject to temperatures above room temperature.

Oxygen must be added to the system in order for the phenylenediamine co-inhibitor to work properly. Oxygen is added separately into the system to achieve a greater concentration of oxygen in the required area. The oxygen employed in the present invention may be in the form of oxygen or an oxygen-containing gas. If an oxygen-containing gas is employed, the remaining constituents of the gas must be inert to the vinyl aromatic compound under the distillation conditions. The most useful and least expensive source of oxygen is air, which is preferred for the present invention. The amount of oxygen may vary widely, but generally it is desirable to use that amount found in air.

Referring to the drawings, FIG. 1 illustrates a conventional styrene distillation train comprising a benzene-toluene fractionation column 10, referred to in the industry as a B-T column, an ethylbenzene or recycle column 12, and a styrene or finishing column 14. It should be noted that the operational principles of the present distillation method are highly suitable for use, with minor modifications, with other distillation equipment used in the purification of other vinyl aromatic compounds. As shown in FIG. 1, a crude styrene feed is introduced into the intermediate portion of B-T column 10 through feedline 16. B-T column 10 may be of any suitable design known to one skilled in the art and may contain any suitable number of vapor-liquid contacting devices, such as bubble cap trays, perforated trays, etc. Usually, however, column 10 contains less than forty distillation trays. Column 10 is also equipped with a suitable reboiler 18 for supplying heat thereto. Temperature of reboiler 18 is generally from about 190° F. to about 250° F.

While most of the polymer is formed in the ethylbenzene or recycle column 12, a small but significant amount of the total polymer formed during distillation is formed in the B-T column 10. Accordingly, a polymerization inhibitor is desirable within this column. To prevent polymerization in the B-T column 10, 2,6-dinitro-p-cresol hereinafter referred to as DNPC, is introduced into the B-T column 10 as a separate stream through line 20, or it may be incorporated into the crude styrene feed flowing through line 16. To facilitate the process, the phenylenediamine inhibitor may also be introduced into the B-T column 10 through line 20 or it may be incorporated into the crude styrene feed flowing through line 16. Although the phenylenediamine inhibotor provides little or no inhibition in B-T column 10 due to lack of oxygen, it is transported with the B-T bottoms through line 24 to the recycle column 12 where it acts as the primary inhibitor therein. When the DNPC and/or phenylenediamine polymerization inhibitor are added to the B-T column 10 as a separate stream they are preferably dissolved in a volatile aromatic hydrocarbon diluent such as ethylbenzene. The position of the inhibitor feedline 20 will normally be intermediate to B-T column 10 in order to achieve an inhibitor distribution which is nearly coincident with the distribution of the readily polymerizable vinyl aromatic compound within the column 10.

Under the distillation conditions imposed in column 10, an overhead stream comprising benzene and toluene is removed via line 22. These low boiling aromatic hydrocarbons are subsequently condensed and passed to storage for further use. The bottoms product in the B-T column comprising styrene, ethylbenzene, inhibitor and tar, serves as a charge to the recycle or ethylbenzene column 12. The bottoms product is introduced into the intermediate portion of ethylbenzene column 12 by means of line 24 and pump 26. The recycle column 12 may be of any suitable design known to those skilled in the art and may contain from 40 to 100 trays. Preferably, however, the recycle column is of the parallel path design. Additionally, it is also preferable that the recycle column contain a large number of trays, as many as 72, in order to achieve a proper separation between the similar boiling styrene and ethylbenzene. The B-T bottoms are preferably introduced into the intermediate portion of the recycle column 12.

A certain amount of inhibitor protection within the ethylbenzene column 12 is provided by the phenylenediamine composition introduced intermediate to column 12 through line 28, together with the B-T bottoms fraction through line 30, or with the DNPC into the B-T column through line 20. It is necessary to add air only to recycle column 12 due to DNPC protection in the rest of the distillation train. In the recycle column 12 a more effective polymerization inhibitor is necessary due to the high temperatures up to 150° C. therein which are desirable in that column for a more energy efficient distillation. By obtaining temperatures of at least 118° C. and preferably 130° C. or more, low pressure steam may be recovered from an overhead condensor (not shown) on recycle column 12.

Oxygen is introduced into reboilers 32 through air purge lines 36 and 38 respectively. Alternatively, oxygen may be introduced into reboilers 32 through sump or boot 40 via line 42 if there is sufficient air pressure/volume to reach the reboilers through line 43. For the phenylenediamine to be effective, an equilibrium amount of oxygen is dissolved in the liquid phase of the column 12; however, the amount of oxygen introduced should not exceed that amount which could cause explosion therein. The oxygen is dispersed throughout the column 12 where it works in conjunction with the phenylenediamine to inhibit polymerization therein. The amount of oxygen necessary will depend on the number and spacing of oxygen inlets around column 12, and how efficiently oxygen and liquid hydrocarbon are mixed therein. Therefore in practical application, the oxygen flow is increased as long as polymer yields are reduced, limited by the amount of oxygen which would yield an explosive mixture. Complete dispersion of air throughout column 12 does not generally occur, therefore the presence of DNPC therein works as a co-inhibitor at those locations where the effectiveness of the phenylenediamine is diminished due to the absence of air. Therefore, the DNPC continues providing polymerization inhibition in those areas of recycle column 12 where there is an absence of air thereby providing an overall higher polymerization inhibition effectiveness than would have been achieved if only phenylenediamine had been present by itself or in combination with other oxygen activated inhibitors.

Surprisingly, it has been found that not only is DNPC compatible with the phenylenediamine, DNPC also works as a polymerization inhibitor in the presence of air as well as in its absence. DNPC therefore also provides inhibitor protection in addition to that provided by phenylenediamine in those areas of the recycle column where there is effective air dispersion. It has been found, however, that when DNPC alone is used as an inhibitor in the presence of air, the DNPC is exhausted more rapidly. This may be due to the fact that more polymer free radicals are generated in the presence of air. Therefore, to maintain effective DNPC/oxygen polymerization inhibition over an extended period of time it is necessary to add more DNPC inhibitor. Additional DNPC and phenylenediamine protection may be obtained by the recycle of tar containing DNPC/phenylenediamine back into recycle column 12 as explained in U.S. Pat. No. 4,272,344.

Alternatively, the phenylenediamine inhibitor may be introduced with the DNPC inhibitor into the B-T column 10 through line 20 as a DNPC/phenylenediamine mixture. There is no preferred order of mixing these togehter. A random order of mixing at ambient temperature and pressure will achieve suitable results. A portion of the DNPC/phenylenediamine inhibitor travels through the B-T column to the recycle column 12 together with the B-T bottoms product.

The bottoms portion from recycle column 12 comprising styrene inhibitor and tar is withdrawn from the reboiler area of recycle column 12 through line 60. The recycle bottoms is then fed by pump 62 into the intermediate portion of the styrene or finishing column 14 through line 64. Optionally, the bottoms material may be introduced into the lower portion of the styrene column 14 through line 66.

The finishing column 14 may be of any suitable design known to those skilled in the art. A typical column will contain for example, about 24 distillation trays. Reboilers 68 are connected to sump 76 through line 78 and pump 80. Reboiler 68 is generally operated at a temperature from about 82° C. to about 121° C. Generally, inhibitor protection is adequately provided in this column by the DNPC and phenylenediamine inhibitor present in the bottoms feed. A portion of the tar from column 14 may be recycled at least back into the ethylbenzene column 12 through line 88 in order to further supplement the DNPC within the system.

The high purity styrene overhead product is withdrawn through line 74 from styrene column 14. The styrene column bottoms product, composed of polystyrene, undistilled styrene, heavy by-products and the DNPC/phenylenediamine co-inhibitor, is withdrawn off the reboiler recirculating line 78 and directed to a flash pot 54 via line 85 for further processing. In the flash pot 84 residual styrene is removed from the bottoms of the styrene column and recycled back thereto through line 86. The tar produced in the flash pot 84 is withdrawn from the system on a continuous basis through line 83 or recycled back to the recycle column 12 or B-T column 10 through line 88.

Figure 2:
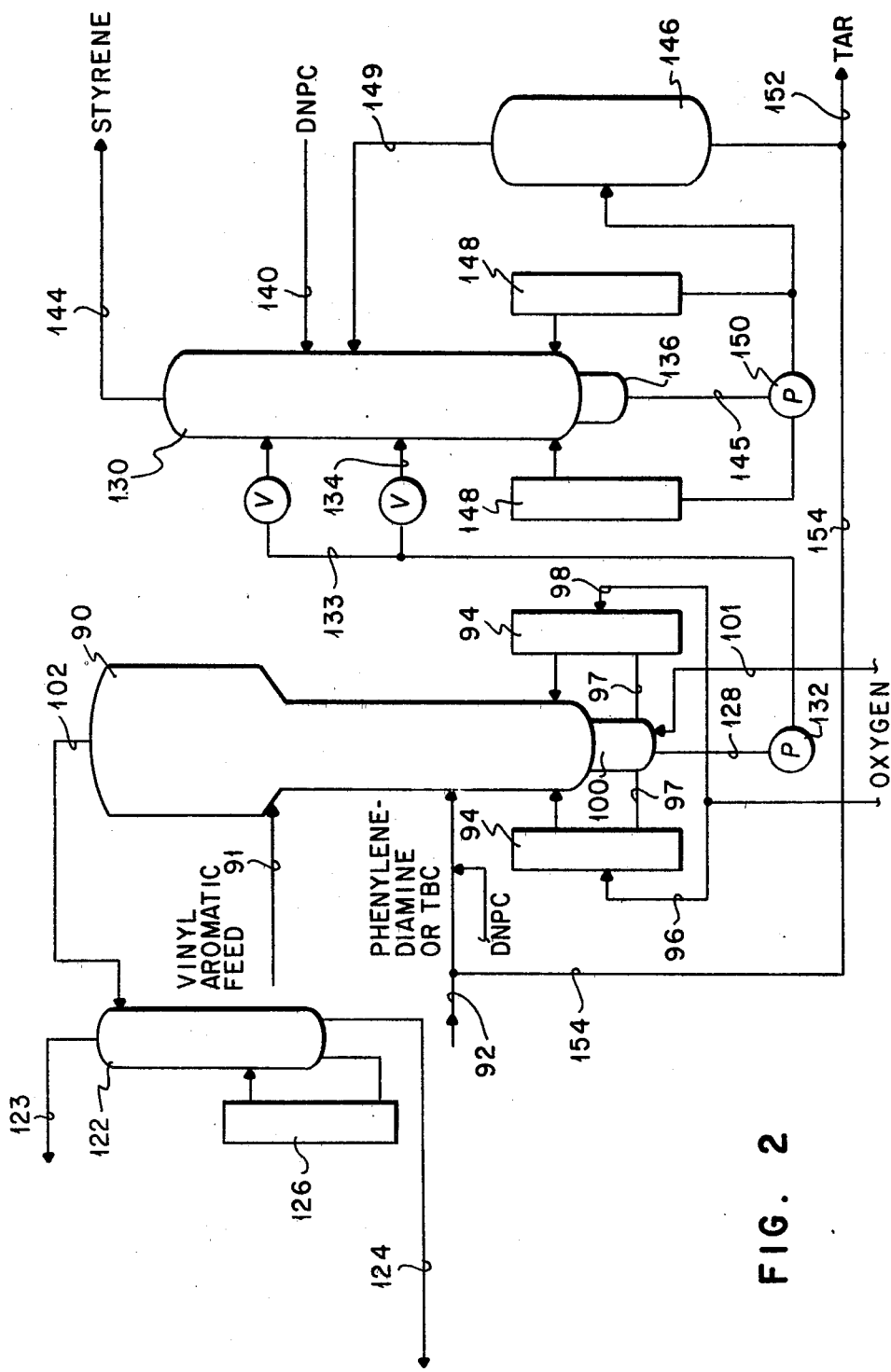
FIG. 2 is a schematic diagram of another embodiment of the process of the present invention utilizing direct injection of the vinyl aromatic feed into the recycle column.

FIG. 2 illustrated the application of the distillation method of the present invention to another typical distillation train. A styrene feed is introduced through line 91 into the intermediate portion of recycle column 90, which is preferably of the parallel distillation path design. Line 92 supplies the phenylenediamine inhibitor to the recycle column 90. Heat is supplied to the bottoms of column 90 by means of reboilers 94. Oxygen is introduced into reboilers 94 through air purge lines 96 and 98. Oxygen may be introduced directly into reboilers 94 through sump or boot 100 and line 101 if there is sufficient oxygen pressure and volume to reach the reboilers through lines 97. In B-T column 122, benzene and toluene are withdrawn as an overhead fraction through line 123 and are subsequently condensed for further use. An ethylbenzene bottoms product is withdrawn through line 124 and is recycled for further use. Reboiler 126 provides B-T column 122 with the necessary heat for distillation.

The recycle bottoms product comprising polystyrene, undistilled styrene, heavy by-products, phenylenediamine and DNPC is withdrawn from recycle column 90 through line 128. The impure styrene fraction is then charged to the upper portion of the styrene column 130 by means of pump 132 and line 133. Optionally, impure styrene may be introduced into the lower region of styrene column 100 through line 134. A reboiler circuit comprising reboiler 136 and pump 138 is attached to the styrene or finishing column 130 for supplying the necessary heat thereto. DNPC is preferably introduced with the phenylenediamine into recycle column 90 through line 92. The purified styrene overhead product is withdrawn through line 144.

Reboilers 148 are connected to finishing column sump 136 through recirculating line 145 and pump 150. The finishing column bottoms produce is withdrawn off reboiler recirculating line 145 for further processing in flash pot 146. Flash pot 146 recycles back into finishing column 14 through line 149. The tar produced during the distillation process is withdrawn through line 152 or recycled back to the distillation train through line 154.

In another embodiment of the present invention, an effective amount of 4-tert-butylcatechol is introduced into the aforementioned distillation trains through recycle columns 12, 90 in place of the phenylenediamine to act as a co-inhibitor with DNPC. It has been found that DNPC and 4-tert-butylcatechol, hereinafter referred to as TBC, is an efficient co-inhibitor system in the presence of air at temperatures up to 140° C. An effective amount of TBC, based on vinyl aromatic feed to the B-T column 10 or the recycle column 90, is from about 50 ppm to about 2000 ppm; a preferred amount of TBC is from about 200 ppm to about 1000 ppm. The preferred ppm ratio of TBC to DNPC is 2 to 3.

Use of the compositions and method of the present invention enables a distillation apparatus to operate with an increased throughput rate as opposed to conventional prior art processes since higher temperatures are permitted in the recycle column due to introduction of effective amounts of DNPC/phenylenediamine or DNPC/TBC inhibitor composition. In addition, the DNPC inhibitor may be used in the remaining fractionation columns to insure effective polymerization inhibition where lower temperatures and absence of air are encountered. Therefore, higher distillation temperatures and higher pressure may be utilized without the formation of objectionable amounts of polymer. In this manner, the rate of distillation may be increased without increasing the amount of polymerization which was previously experienced in the conventional distillation procedures.

In addition by optimizing the distribution of the DNPC/phenylenediamine or DNPC/TBC inhibitor within the recycle column and by optimizing the distribution of DNPC inhibitor in the remaining fractionation columns of the distillation train, greater temperatures may be achieved in the recycle column than in conventional distillation procedures to permit more efficient energy recovery therefrom.

In order to more fully describe the present invention, the following examples are presented which are intended to be illustrative and not in any sense limitative of the invention.

EXAMPLE 1

Two 100 ml reaction flasks were prepared. A first (1) was charged with 25 grams styrene to which was added 100 ppm DNPC and 50 ppm Flexone 4L, (a trademark of Uniroyal Chemical, Flexone 4L having the chemical formula N,N'-Bis(1,4-dimethylpentyl)-p-phenylenediamine as discussed in the Uniroyal Material Safety Sheet covering Flexone 4L, and incorporated herein by reference.) A second (2) flask was charged with 25 grams styrene to which was added 200 ppm DNPC. The flasks were fitted with magnetic stirrers and septum closures and heated in a stirred oil bath to 138° C. plus or minus 2° C. The first flask was purged with approximately 3 ml/min air run beneath the liquid surface during the period of distillation. The second flask was run under a nitrogen blanket. After two hours the samples were tested for the degree of styrene polymerization as a check, by measuring the changes in refractive index. As a check, occasionally the monomer was stripped off and the remaining polymer weighed. A final polymer yield of 14.94% resulted in the first flask, whereas a final polymer yield of 18.24% resulted in Flask 2, indicating the superior inhibitory effectiveness at high temperature of the phenylenediamine/DNPC co-inhibitor system over the DNPC alone.

EXAMPLE 2

A 100 ml reaction flask was charged with 25 grams styrene to which was added 100 ppm DNPC and 90 ppm TBC. The flask was fitted with a magnetic stirrer and septum closure and heated in a stirred oil bath to 118° C. plus or minus 2° C. The flask was purged with 1–2 ml/minute of air run beneath the liquid surface during the period of heating. The following results were obtained:

| time (minutes) | % polymerization |
| --- | --- |
| 0 | 0 |
| 60 | 0.34 |
| 120 | 0.42 |
| 150 | 0.58 |
| 180 | 0.75 |
| 210 | 1.23 |

Comparison Example 2A

A 100 ml flask was charged with 25 grams styrene to which was added 100 ppm DNPC. The procedure of Example 2 was followed and the following results were obtained:

| time (minutes) | % polymerization |
| --- | --- |
| 0 | 0 |
| 60 | 0.50 |
| 120 | 12.52 (DNPC consumed) |

Comparison Example 2B

A 100 ml flask was charged with 25 grams styrene to which was added 90 ppm TBC. The procedure of Example 2 was followed and the following results were obtained:

| time (minutes) | % polymerization |
| --- | --- |
| 0 | 0 |
| 60 | 1.15 |
| 120 | 1.71 |
| 150 | 1.71 |
| 180 | 2.60 |
| 210 | 9.29 |

The results of Example 2 and Comparison Examples 2A and 2B indicate the increased effectiveness of the DNPC/TBC co-inhibitor composition at lower temperatures over DNPC or TBC alone.

EXAMPLE 3

A 12" diameter pilot plant fractionation column packed with Norton Intalox Packing was utilized to distill a 1:1 mixture of ethylbenzene and styrene. The column had a continuous feed and overhead draw to simulate a conventional recycle column. 300 ppm of DNPC (based on styrene content) and 200 ppm of Flexzone 4L (based on styrene content) was introduced into the column. Air was introduced into the column at a rate of 1.2 liters/minute. The reboiler temperature was maintained at 118° C. Bottoms were drawn off every 30 to 60 minutes to maintain a cnstant reboiler level. At hourly intervals, the feed rate, overhead rate, column temperature profile, reflux ratio and overhead pressure were recorded. At 2 hour intervals, bottom and overhead samples were collected. At 6 to 8 hour intervals, aldehyde and peroxide content in the overhead were determined. The percent polymer in the bottoms was determined by vacuum evaporating a portion of the bottoms to dryness, placing a portion of the bottoms product in a flask, heating the flask to drive off the monomer, and then weighing the remaining amount which comprises polymer.

The following results were obtained:
Polymer Yield: 0–0.21%
Aldehydes: 181–427 ppm
Peroxides: 13–25 ppm As a further test, the oxygen rate was decreased from 0.50 to 0.25 liters/minutes, then to 0.10 liters/minutes; the polymer yield ranged from 0.24 to 0.36%.

EXAMPLE 4

The procedure of Example 3 was followed utilizing 300 ppm DNPC and 200 ppm TBC. The reboiler temperature was maintained at 118° C.

The following results were obtained:
Polymer Yield: 0.80–1.22%
Aldehydes: 220–420 ppm
Peroxides: 25–141 ppm As a further test, the oxygen flow rate was decreased from 0.50 to 0.25 liter/min then to 0.10 liter/min; the polymer yield steadily increased from 1.29 to 2.09%.

Comparison Example 3/4

The procedure of Example 3 was followed except no air was introduced to the column and 500 ppm DNPC alone was utilized as an inhibitor. The reboiler was maintained at 118° C. The polymer yield ranged from 3.97 to 4.25%.

EXAMPLE 5

The procedure of Example 3 was followed utilizing 300 ppm DNPC and 200 ppm Flexzone 4L (the same concentrations used at 118° C. in Example 3). The reboiler temperature was maintained at 132° C.

The following results were obtained:
Polymer Yield: 0.80–1.22%
Aldehydes: 280–346 ppm
Peroxides: 48–80 ppm As a further test, the oxygen flow rate was decreased from 0.50 to 0.25 liter/min, then to 0.10 liter/min; as a result the polymer yield increased slightly from 1.24 to 1.47%.

EXAMPLE 6

The procedure of Example 3 was followed utilizing 600 ppm DNPC and 400 ppm TBC. (Double the concentrations used at 118° C. in Example 4.) Reboiler temperature was maintained at 132° C.

The following results were obtained:
Polymer Yield: 1.01–1.36%
Aldehydes: 310–440 ppm
Peroxides: 107–167 ppm As a further test, the oxygen flow rate was decreased from 0.50 to 0.25 liter/min, then to 0.10 liter/min; as a result the polymer yield steadily increased from 1.57 to 2.92%.

Comparison Example 5/6

The procedure of Example 3 was followed utilizing 1000 ppm DNPC alone as an inhibitor. (Double the concentration of DNPC used at 118° C. in Comparison Example 3/4.)

The following results were obtained:
Polymer Yield: 2.70–3.00%
Aldehydes: 220–260 ppm
Peroxides: 49–96 ppm While the present invention has been described in various preferred embodiments and illustrated by numerous exaples, a skilled artist will appreciate that various modifications, substitutions, omissions and changes may be made without departing from the spirit thereof.

The embodiments of the invention in which an exclusive property or privilege is claimed is defined as follows:

1. A process for inhibiting the polymerization of a vinyl aromatic compound, comprising subjecting the vinyl aromatic compound when heated to effective amounts of 2,6-dinitro-p-cresol and a phenylenediamine, respectively, in the presence of oxygen, the phenylenediamine having the formula

wherein R₁ and R₂ are alkyl, aryl or hydrogen.

2. The process of claim 1 wherein the vinyl aromatic compound is selected from the group consisting of styrene, substituted styrene, divinylbenzene, vinyl toluene, vinyl naphthalene, the polyvinylbenzenes, and structural isomers thereof.

3. The process of claim 1 wherein the alkyl groups contain from 1 to 12 carbons respectively.

4. The process of claim 1 wherein the vinyl aromatic compound is heated to a temperature up to 150° C.

5. The process of claim 1 wherein
 (a) the effective amount of 2,6-dinitro-p-cresol is from about 100 ppm to about 2000 ppm; and
 (b) the effective amount of phenylenediamine is from about 50 ppm to about 2000 ppm.

6. The process of claim 1 wherein the heating of the vinyl aromatic compound occurs during distillation of said compound.

7. A process for inhibiting the polymerization of a vinyl aromatic compound, comprising subjecting the vinyl aromatic compound when heated to effective amounts of 2,6-dinitro-p-cresol and 4-tert-butylcatechol respectively, in the presence of oxygen.

8. The process of claim 7 wherein the vinyl aromatic compound is selected from the group consisting of styrene, substituted styrene, divinylbenzene, vinyl toluene, vinyl naphthalene, the polyvinylbenzenes, and structural isomers thereof.

9. The process of claim 7 wherein the vinyl aromatic compound is heated to a temperature up to of 140° C.

10. The process of claim 7 wherein
 (a) the effective amounts of 2,6-dinitro-p-cresol is from about 100 ppm to about 2000 ppm based on vinyl aromatic going to purification; and
 (b) the effective amount of 4-tert-butylcatechol is from about 50 ppm to about 2000 ppm based on vinyl aromatic feed.

* * * * *